(12) United States Patent
Völlm et al.

(10) Patent No.: US 9,498,777 B2
(45) Date of Patent: Nov. 22, 2016

(54) CELLS HAVING CAVITIES AND THE MANUFACTURE AND USE OF THE SAME

(75) Inventors: Henning Völlm, Hermeskeil (DE); Ulrich Schmid, Saarbrücken (DE); Andreas Schütze, St. Ingbert (DE); Helmut Seidel, Starnberg (DE); Dara Feili, Saarbrücken (DE)

(73) Assignee: Henning Völlm, Hermeskeil (DE)

( * ) Notice: Subject to any disclaimer, the term of this patent is extended or adjusted under 35 U.S.C. 154(b) by 605 days.

(21) Appl. No.: 12/694,030

(22) Filed: Jan. 26, 2010

(65) Prior Publication Data
US 2010/0189605 A1 Jul. 29, 2010

Related U.S. Application Data

(63) Continuation of application No. PCT/EP2008/005878, filed on Jul. 17, 2008.

(30) Foreign Application Priority Data

Jul. 26, 2007 (DE) .......................... 10 2007 034 963

(51) Int. Cl.
*B01L 3/00* (2006.01)
*G04F 5/14* (2006.01)
*H03L 7/26* (2006.01)
*G01N 21/03* (2006.01)

(52) U.S. Cl.
CPC .......... *B01L 3/508* (2013.01); *B01L 2200/148* (2013.01); *B01L 2300/0654* (2013.01); *B01L 2300/10* (2013.01); *G01N 21/0303* (2013.01); *G04F 5/14* (2013.01); *H03L 7/26* (2013.01);
(Continued)

(58) Field of Classification Search
CPC ................................. G04F 5/14; B01L 3/508
USPC .................. 422/62, 557, 547; 428/34.4, 38;
220/582, 662, 665; 359/894; 73/52;
(Continued)

(56) References Cited

U.S. PATENT DOCUMENTS 6,265,945 B1 * 7/2001 Delaney et al. ................... 331/3
6,570,459 B1 * 5/2003 Nathanson et al. ......... 331/94.1
6,900,702 B2 * 5/2005 Youngner et al. ........... 331/94.1
(Continued)

FOREIGN PATENT DOCUMENTS

DE 692 05 307 T2 5/1996
DE 696 29 483 T2 7/2004

OTHER PUBLICATIONS

J. Kitching et al., "Miniature Vapor-Cell Atomic-Frequency References," Applied Physics Letters, vol. 81, No. 3, Jul. 15, 2002, pp. 553-555.
(Continued)

*Primary Examiner* — Jill Warden
(74) *Attorney, Agent, or Firm* — Hanley, Flight & Zimmerman, LLC

(57) ABSTRACT

Cells having cavities and the manufacture and use of the same are described. An example cell includes a first layer including a gap to at least partially define a cavity and a reservoir area to receive material to enter the cavity by diffusion. Additionally, the cell includes one or more other layers coupled to the first layer to at least partially define the cavity and to hermetically seal the cavity from an exterior environment.

24 Claims, 2 Drawing Sheets

(52) U.S. Cl.
CPC ............. *Y10T 156/10* (2015.01); *Y10T 428/13* (2015.01); *Y10T 428/131* (2015.01)

(58) Field of Classification Search
USPC ............. 206/486, 493; D10/40; 331/3, 94.1; 429/57, 515, 516
See application file for complete search history.

(56) References Cited

U.S. PATENT DOCUMENTS

| | | | |
|---|---|---|---|
| 7,619,485 B2* | 11/2009 | DeNatale et al. | ............ 331/94.1 |
| 7,701,302 B2* | 4/2010 | Koyama | ............ 331/94.1 |
| 2005/0184815 A1* | 8/2005 | Lipp et al. | ............ G04F 5/14 |
| | | | 331/94.1 |
| 2005/0236460 A1* | 10/2005 | Abbink et al. | ............ 228/101 |
| 2006/0022761 A1 | 2/2006 | Abeles et al. | |
| 2006/0030483 A1 | 2/2006 | Jang | |
| 2010/0055885 A1* | 3/2010 | Robinson et al. | ............ 438/510 |

OTHER PUBLICATIONS

Patent Cooperation Treaty, "International Search Report," issued by the International Searching Authority in connection with related PCT application No. PCT/EP2008/005878, mailed Jan. 20, 2009 (4 pages).

Patent Cooperation Treaty, "Written Opinion of the International Searching Authority," issued by the International Searching Authority in connection with related PCT application No. PCT/EP2008/005878, mailed Feb. 24, 2010 (8 pages).

International Bureau, "International Preliminary Report on Patentability," issued in connection with PCT application Serial No. PCT/EP2008/005878, issued Feb. 24, 2010 (9 pages).

Liew et al., "Microfabricated alkali atom vapor cells," Applied Physics Letters, vol. 84, No. 14, Apr. 5, 2004, (3 pages).

* cited by examiner

CELLS HAVING CAVITIES AND THE MANUFACTURE AND USE OF THE SAME

RELATED APPLICATION

This patent is a continuation of International Patent Application Serial No. PCT/EP2008/005878, filed Jul. 17, 2008, which claims priority to German Patent Application 10 2007 034 963.9, filed on Jul. 26, 2007, both of which are hereby incorporated herein by reference in their entireties.

FIELD OF THE DISCLOSURE

This patent relates generally to cells having cavities and, more specifically, to cells having cavities and the manufacture and use of the same.

BACKGROUND

Cells having cavities, such as vapor cells, may be used in different industrial and/or scientific applications. Some applications in which these types of cells may be utilized include physics (e.g., experimental physics), biotechnology, space research or lab on a chip applications.

Vapor cells containing or filled with a reactive gas may be used as a resonator element in atomic clocks to provide a time standard. In atomic clock applications, hyperfine structure transition of gaseous alkali metals such as cesium or rubidium provide a high precision frequency or time standard.

While known methods of inducing hyperfine structure transition include using microwave radiation, another method of inducing hyperfine structure transition, known as coherent population trapping (CPT), uses optically induced resonance instead. In contrast to inducing hyperfine structure transition using microwave radiation, CPT enables significant miniaturization of reactive gas-filled vapor cells and its corresponding components, thereby enabling the associated atomic clocks to be built smaller (e.g., miniaturized) as well. Miniaturized atomic clocks are popular especially for non-stationary uses even though these atomic clocks may have relatively lower accuracy.

Miniaturized atomic clocks and their corresponding miniaturized vapor cells may be utilized in non-stationary equipment applications for satellite navigation systems (e.g., GPS, GLONAA, or Galileo). As compared to other approaches that require signals from four satellites to determine a position of an object, implementing satellite navigation systems with miniaturized atomic clocks enable a relatively more accurate position of an object to be determined based on signals from only three satellites.

In other applications, miniaturized atomic clocks and their corresponding miniaturized vapor cells may be used to enable the synchronization of signals in communication networks or cryptography keys. Additionally, vapor cells filled with reactive gas may be utilized in high-precision magnetic field sensors or rotational speed sensors of nuclear magnetic resonance gyroscopes (NMRG).

Macroscopic vapor cells may be manufactured using fine machining techniques such as, individually filling glass capsules with a desired material and then carefully closing the glass capsules using glass welding or glassblowing techniques. Hermetic bonding or sealing of silicon and/or glass may be utilized during the manufacturing of microscopic vapor cells. However, similar to the manufacturing process of macroscopic vapor cells in which these vapor cells are filled prior to closing, microscopic vapor cells must be filled with the desired material prior to hermetic sealing.

U.S. patent publication number 2006/0022761 relates to a process of manufacturing vapor cells (e.g., vapor gas cells) filled with cesium. In the process described, using processes known from semiconductor technology, a penetrating hole is etched in a silicon wafer that corresponds to the interior dimensions of the vapor cell. The silicon wafer is then connected to a glass wafer using anodic bonding to close the penetrating hole. In a cavity created during etching, fluid cesium is then introduced into a nitrogen or argon atmosphere. Thereafter, the cavity is hermetically sealed by another glass wafer using anodic bonding. The gas enclosed in the cavity (e.g., argon or nitrogen) acts as a buffer gas during the use of the vapor cell.

U.S. Pat. No. 6,900,702 B2 relates to a process of introducing rubidium into a vapor cell that is a component of a frequency standard based on silicon wafers. Once the rubidium is introduced into the vapor cell, the vapor cell is sealed.

Both U.S. patent publication number 2006/0022761 and U.S. Pat. No. 6,900,702 B2 also describe changing a vapor pressure within the vapor cells by heating the sealed vapor cells and the alkali metals contained therein with a laser or other heating element.

The publication, Li-Anne Liew et al. in Appl. Phys. Lett. Vol. 84 no. 14 dated Apr. 5, 2004, describes an alternative approach of filling vapor cells (e.g., vapor pressure cells) using wafers. Instead of filling the vapor cell with pure cesium, cesium chloride and barium azide are introduced into the vapor cell and then the vapor cell is sealed. After sealing, a chemical reaction between the cesium chloride and the barium azide may be initiated that yields atomic cesium.

The processes described above have disadvantages that prevent cost effective production. For example, alkali metals such as cesium and rubidium are very reactive with, for example, water vapor and oxygen, requiring a protected atmosphere when handling. Therefore, when filling vapor cells with these alkali metals, special systems and significant care must be taken to ensure safety.

As mentioned above, barium azide may be used in processes based on reactive gas formation by chemical reaction taking place within the vapor cell. However, azides and particularly barium azide are highly dangerous substances that may be used as explosives. Because azides cannot be handled or transported in Europe, these substances are essentially unavailable.

Reference is also made to patent publications DE 692 05 307 T2 and DE 696 29 483 T2.

DETAILED DESCRIPTION

Certain examples are shown in the above-identified figures and described in detail below. In describing these examples, like or identical reference numbers are used to identify similar or the same elements. The figures are not necessarily to scale and certain features and certain views of the figures may be shown exaggerated in scale or in schematic for clarity and/or conciseness. Additionally, several examples have been described throughout this specification. Any features from any example may be included with, a replacement for, or otherwise combined with other features from other examples.

The example methods, manufacturing processes and apparatus described herein relate to cells having a cavity and a wall(s) or surface(s) surrounding the cavity. The wall(s) provides at least one deposit area to enable material (e.g., rubidium, cesium) to enter the cavity by diffusion. The wall(s) contains a portion in which a gap, recess or aperture can be defined. Additionally, the wall(s) may provide one or more deposit or reservoir areas from which material may be transferred into the gap and/or cavity by diffusion.

The cells described herein may be used as a time or frequency standard. Additionally or alternatively, controlled diffusion of a material(s) corresponding to a reactive gas(es) from the deposit area of the cells may be utilized to obtain a predetermined or particular concentration of gaseous material in the cavity of the respective cell.

Figure 1:
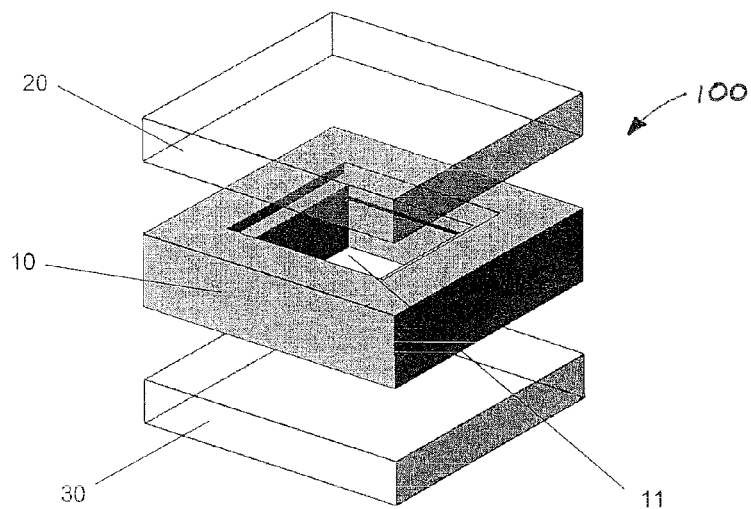
FIG. 1 depicts an exploded view of an example cell.
Figure 2:
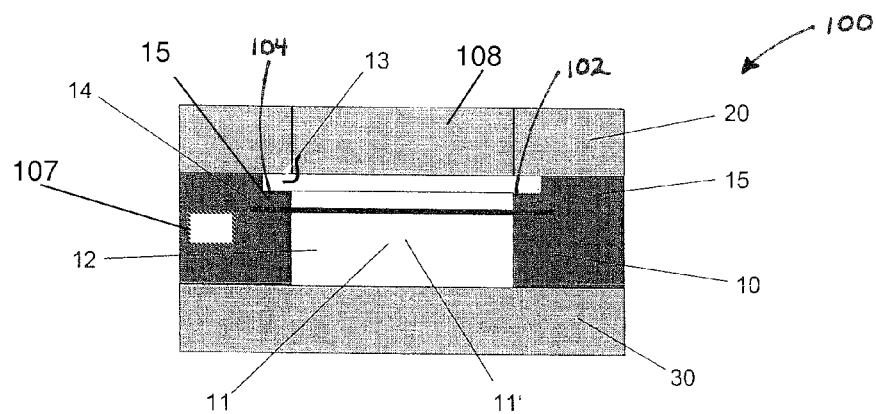
FIG. 2 depicts a different view of the example cell of FIG. 1.
Figure 3:
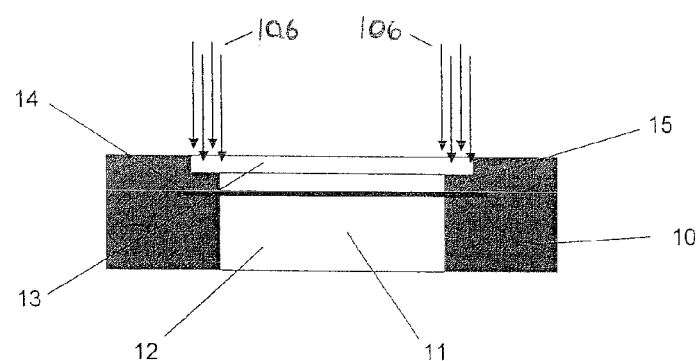
FIG. 3 depicts a portion of the example cell of FIG. 1.

FIGS. 1-3 depict a cell 100 that includes a first layer, portion, wall segment, flat or substrate 10, a second layer, portion, wall segment, flat or substrate (e.g., cover layer) 20 and a third layer, portion, wall segment, flat or substrate (e.g., cover layer) 30. A gap or aperture 11 extends through the first layer 10. While the gap 11 depicted in FIG. 1 is a square gap, the gap 11 can be any other shape or form instead.

The second and third layers 20 and 30 are to be positioned on either side of the first layer 10 and the gap 11, thereby defining a hollow space, chamber or cavity 11' within the cell 100. The interaction between the first, second and third layers 10, 20 and 30 define a perimeter, barrier or wall of the cell 100 and/or the cavity 11' that seals (e.g., hermetically seals) the cavity 11' from the atmosphere (e.g., exterior space). Specifically, the cavity 11' is defined by a plurality of surfaces or walls of the first, second and third layers 10, 20 and 30.

The first layer 10 may be made of silicon, a silicon material or any other suitable material(s) such as materials used in microelectronics (e.g., structured ceramics, glass ceramics) or used in semiconductors (e.g., semi-conductor substrate), for example. The second and third layers 20 and 30 may be made of a translucent material such as glass that enables optical access to an interior of the cell 100.

The gap 11 may be formed by any suitable process such as a mechanical process(es) or by a photolithographic etching process(es) known in the semiconductor industry. The gap 11 includes a first portion or partial area 12 adjacent to a second portion or partial area 13. Because the first and second portions 12 and 13 have different cross-sections, a step 102 is formed adjacent the transition between the portions 12 and 13. The step 102 may be formed using any suitable process such as two sequential etching processes, for example.

Turning to FIG. 2, a diffusion barrier 14 is depicted substantially within the cell 100. While the diffusion barrier 14 may be positioned in other arrangements or orientations, as depicted in FIG. 2, the diffusion barrier 14 is substantially parallel to a surface 104 of the step within the first layer 10.

The cell 100 includes a reservoir area 15 within the first layer 10 that may be positioned between the step 102 (e.g., the surface 104 of the step 102) and the diffusion barrier 14. The reservoir area 15 may receive deposits of a reactive gaseous material(s). Because of the diffusion barrier 14, the reactive gaseous material deposited within the reservoir area 15 may diffuse toward the sides into the cavity 11' or in a direction away from the diffusion barrier and into the cavity 11' (e.g., toward the second layer 20 and/or the second portion 13).

FIG. 3 depicts a process of exposing the reservoir area 15 to ion ray(s) 106 of a desired reactive gaseous material(s) to enrich or deposit (e.g., ion implantation) the reactive gaseous ions within the reservoir area 15. Commercially available apparatus may be utilized during the ion implantation processes. The process(es) of exposing the reservoir area 15 to the ion ray(s) 16 takes place prior to coupling, attaching or joining the first layer 10 with the second and third layers 20 and 30.

By depositing the reactive gaseous material into the reservoir area 15 using ion implantation processes, reactions between the reactive gaseous material and the atmosphere are substantially eliminated, because ion implantation processes take place in a vacuum and the reactive gaseous material(s) are initially presented in the relatively stable form of a chemical compound.

After ion implantation, the second and third layers 20 and 30 are coupled or joined to the first layer 10 to seal (e.g., hermetically seal) off the cavity 11' from the atmosphere, for example. In contrast to known approaches in which special safety precautions need to be taken when sealing the cells to prevent chemical reactions of the reactive material, such special safety precautions are not or may not be as applicable when practicing the examples described herein.

Anodic wafer bonding has been identified as a practical technique for coupling or joining the first, second and third layers 10, 20 and 30 together. If the cell (e.g., gas cell) 100 contains a buffer gas such as nitrogen or argon in addition to the reactive gaseous material, the cell 100 may be exposed to the atmosphere when sealing and while the first layer 10 is coupled or joined to the second and third layers 20 and 30.

Figure 4:
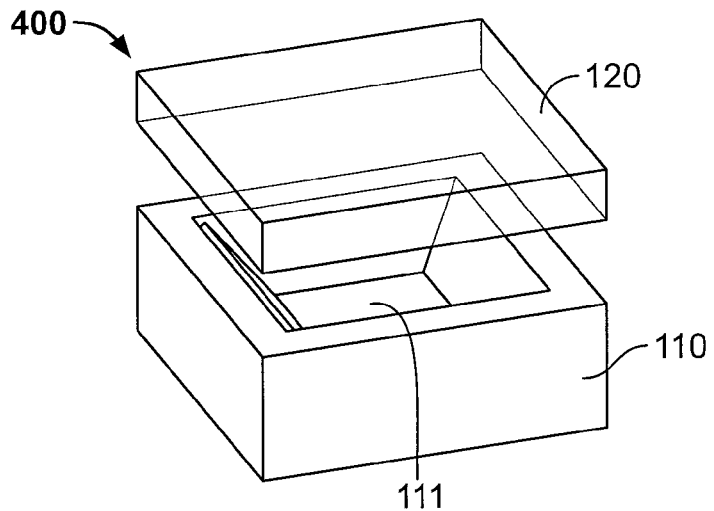
FIG. 4 depicts an exploded view of another example cell.
Figure 5:
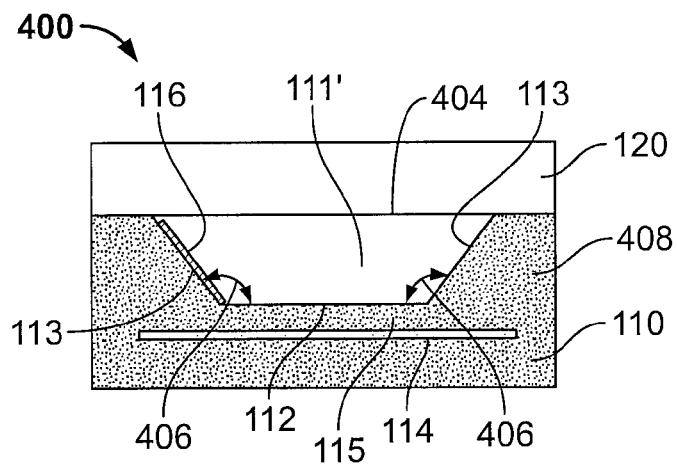
FIG. 5 depicts a different view of the example cell of FIG. 4.
Figure 6:
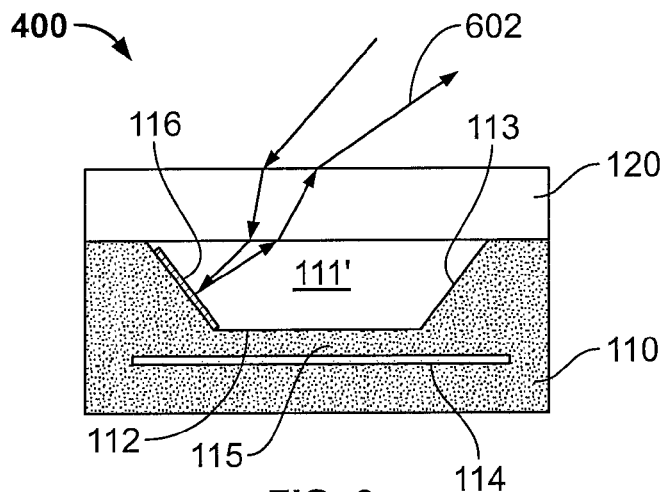
FIG. 6 depicts a light ray entering and reflecting within the example cell of FIG. 4.

FIGS. 4-6 depict an alternative cell 400 that includes a first layer, portion, wall segment, substrate layer or level 110 and a second layer, portion, wall segment, substrate layer or level (e.g., cover layer) 120. The first layer 110 defines a gap or a recess 111. In contrast to the gap 11 described above that extends through the first layer 10, the gap 111 does not extend completely through the first layer 110. The second layer 120 is to be positioned adjacent (e.g., on top of) the first layer 110 and the gap 111, thereby defining a hollow space, chamber or cavity 111' within the cell 400.

The cavity 111' is defined by a plurality of surfaces or walls of the first and second layers 110 and 120. Specifically, the cavity 111' is defined by a surface 404 of the second layer 120, a surface or floor 112 of the first layer 110 and side walls 113 of the first layer 110. In this example, the side walls 113 extend from the surface 112 at opposing angles 406 toward the second layer 120 such that the surface 112 defining the cavity 111' is relatively smaller than the surface 404 defining the cavity 111' and/or the cavity 111' extends toward the second layer 120. The angle 406 may be associated with the grid structure of the substrate material in wet chemical etching processes.

Turning to FIG. 5, a diffusion barrier 114 is depicted substantially within the cell 100. While the diffusion barrier 114 may be positioned in other arrangements or orientations, as depicted in FIG. 5, the diffusion barrier 114 is at a distance from the surface 112 within the first layer 110.

The cell 400 includes a reservoir area 115 within the first layer 110 that may be positioned between the surface 112 and the diffusion barrier 114. Similar to the reservoir area 15 discussed above, the reservoir area 115 may receive deposits of a reactive gaseous material(s).

The second layer 120 may be made of an optically translucent material such as glass, for example. A reflective layer 116 may be positioned adjacent one or more of the side walls 113 to enable light rays entering the cavity 111' through the second layer 120 to be reflected back toward the second layer 120 and detected by a sensor (not shown) outside of the cavity 111'. FIG. 6 depicts an example path 602 of a light ray entering the cavity 111' and being reflected off of the reflective layer 116.

While not shown, in other examples, a diffusion barrier (similar to the diffusion barrier 114) and a corresponding reservoir area (similar to the reservoir area 115) may be provided in an area or portion 408 adjacent to the side wall 113. In such examples, a reflective layer (similar to the reflective layer 116) may be positioned adjacent to the surface 112.

As described above, the reservoir area 115 may be enriched with a material (e.g., a reactive gaseous material) by ion implantation that is to be subsequently diffused. After the reservoir area 115 has been enriched with the material, the first and second layers 110 and 120 may be coupled or joined using anodic bonding to seal (e.g., hermetic sealing) the cavity 111' from the atmosphere, for example.

To enable diffusion of the reactive gaseous material from the reservoir area 15 or 115, the reactive gaseous material may be heated using a heating element (not shown) that is external from the cell 100 or 400 or integrated into the cell 100 or 400, for example. Heating the reactive gaseous material enables the reactive gaseous material to diffuse from the reservoir area 15 or 115 to the cavity 11' or 111', thereby providing a desired pressure of the reactive gaseous material within the cavity 11' or 111'. As the reactive gaseous material diffuses from the reservoir area 15 or 115, the diffusion barrier 14 or 114 substantially prevents the diffusion of the reactive gaseous material into the structure (e.g., substrate structure, the layers 10, 20, 30, 110, 120) itself, thereby urging or providing a preferred route of travel for the diffused reactive gaseous material toward and/or into the cavity 11' or 111' (e.g., controlling the diffusion of the material into the cavity 11' or 111').

The example methods, processes of manufacturing and apparatus described herein relate to cells to be filled with gas (e.g., a reactive gaseous material).

As described above, the cell 100 and/or 400 including the layers 10, 20, 30, 110 and/or 120 define the cavity 11' and/or 111'. Surfaces or walls of the layers 10, 20, 30, 110 and/or 120 surround the cavity 11' and/or 111' and include one or more reservoir areas 15 and/or 115 to enable material (e.g., a reactive gaseous material) to enter the cavity 11' and/or 111' by diffusion. The reservoir area 15 and/or 115 is positioned within one or more of the layers 10, 20, 30, 110 and/or 120 to enable certain materials transferable via diffusion to be collected and/or stored adjacent to and/or within the reservoir area 15 and/of 115. The first layer 10 and/or 110 may be a substrate material used in the semiconductor industry and/or microtechnology; however, other suitable materials may be used instead.

The material deposited within the reservoir area 15 and/or 115 may diffuse into the cavity 11' and/or 111' during a subsequent manufacturing process (e.g., heating), for example.

The layers 10, 20, 30, 110 and/or 120 may seal the cavity 11' and/or 111' from the environment (e.g., exterior environment) and/or the atmosphere. The material moving and/ or diffusing from the reservoir area 15 and/or 115 into the cavity 11' and/or 111' is preferably gaseous and/or in a gaseous state.

The cavity 11' and/or 111' is preferably optically accessible to light entering or impinging from the outside. To enable light accessibility, one or more of the layers 10, 20, 30, 110 and/or 120 includes a portion or area that is at least partially translucent and may be made of glass, for example. In some examples, the cell 100 and/or 400 includes at least two layers (e.g., the layer 10, 20, 30, 110 and/or 120) of substrate material at least one of which may include a translucent area.

Preferably, light rays can pass through the cell 100 and/or 400 in a continuous path of the rays. The cavity 11' and/or 111' may be defined by at least two layers (e.g., sealing cover, translucent material, the layer 10, 20, 30, 110 and/or 120) of substrate material. At least one of layers (e.g., the layer 10, 20, 30, 110 and/or 120) may include a translucent area. The first layer 10 and/or 110 may be made of a silicon material, a structured ceramic material or a structured glass ceramic compound material; however, any other suitable material may be used instead. One or more of the layers 10, 20, 30, 110 and/or 120 may include or be at least partially made of a metal material.

In some examples, light may be reflected off of at least one of the side walls 113 of the cavity 111'. The light may enter the cavity 111' at a first angle and the light may be reflected from or out of the cavity 11' and/or 111' at a second angle different from the first angle. The deflection between the angle of the light entering the cavity and the reflected light may be large or small (e.g., a large or small deflection angle).

The light to enter the cell 100 and/or 400 may be any range within the electromagnetic spectrum such as wavelength ranges bordering the visible light spectrum or invisible wavelengths, for example. The translucent areas or portions of the layer(s) (e.g., the layer 10, 20, 30, 110 and/or 120) may be configured, adapted and/or designed for the penetration of wavelengths of the particular electromagnetic radiation provided (e.g., the electromagnetic radiation to be used with the cell 100 and/or 400).

The cell 100 and/or 400 includes a plurality of substrate layers (e.g., the layers 10, 20, 30, 110 and/or 120) and preferably two or three layers (e.g., the layers 10, 20, 30, 110 and/or 120). As shown in FIGS. 1-3, when the cell 100 includes three layers (e.g., the layers 10, 20 and 30), the cavity 11' may be positioned in the middle of these three layers (e.g., the layers 10, 20 and 30). Specifically, the second and third layers 20 and 30 may cover the first layer 10 on either side to seal the cavity 11' from exterior space or the atmosphere. As shown in FIGS. 4-6, when the cell 400 includes two layers (e.g., the layers 110 and 120), the cavity 111' may be positioned or defined by the first layer 110 and the second layer 120 may cover or be positioned adjacent to the first layer 110 to seal the cavity 111' from exterior space or the atmosphere.

As discussed above, the layers 10, 20, 30, 110 and/or 120 may be coupled and/of firmly fastened together to form the walls or structure of the cell 100 and/or 400.

To utilize advantages associated with metallic materials, one or more of the layers 10, 20, 30, 110 and/or 120 may include or be at least partially made of a metal material. However, preferably, one or more of the layers 10, 20, 30, 110 and/or 120 may be made of material(s) used in semi-conductor technology, microtechnology and/or microelectronics. Materials that may be used include silicon and/or glass, for example. Utilizing such materials enables joining processes at the wafer level such as anodic bonding and/or anodic wafer bonding technology to be used when joining and/or coupling the respective layers 10, 20, 30, 110 and/or 120 together.

The first layer 10 and/or 110 or a portion of the first layer 10 and/or 110 surrounding the cavity (e.g., microcavity) 11' and/or 111' may be made of a structured ceramic material or a structured glass ceramic compound material, for example.

As discussed above, the cell 100 and/or 400 may include or be equipped with a heating structure or element (not shown) integrated into one or more of the layers 10, 20, 30 110 and/or 120 or be adjacent or next to one or more of the layers 10, 20, 30, 110 and/or 120.

The material deposited in the reservoir area 15 and/or 115 may include or be substances that are reactive with the atmosphere. Some materials may include rubidium or cesium, for example.

To substantially prevent the diffusion of the material deposited in the reservoir area 15 and/or 115 in a direction away from the cavity 11' and/or 111', one or more diffusion barriers 14 and/or 114 may be positioned adjacent to or border the reservoir area 15 and/or 115.

The cell 100 and/or 400 may include the layer 10, 20, 30, 110 and/or 12 that defines and/or includes the gap 11 and/or 111 and one of more reservoir areas 15 and/or 115. The reservoir areas 15 and/or 115 may be formed to accept material that, after the introduction into the reservoir area 15 and/or 115 and the formation of the gap 11 and/or 111, diffuses from the reservoir area 15 and/or 115 into the gap 11 and/or 111. After diffusing from the reservoir area 15 and/or 115 and into the gap 11 and/or 111, the material may be present in the gap 11 and/or 111 in a gaseous form and/or state.

A process of manufacturing the cell 100 and/or 400 having the cavity 11' and/or 111' and/or a wall and/or surfaces (e.g., portions or surfaces of the layers 10, 20, 30, 110 and/or 120) surrounding the cavity 11' and/or 111' includes depositing material into one or more of the walls and/or layers 10, 20, 30, 110 and/or 120. The deposited material can then be introduced into the cavity 11' and/or 111' by diffusion.

The process of ion implantation may be utilized to deposit the material (e.g., diffusible material) and/or additional materials into the reservoir area 15 and/or 115. Such an approach of utilizing ion implantation is a particularly suitable commercially available process because the process takes place in a vacuum, which prevents reactions between the deposited material and/or its gas acting as a reagent and the atmosphere (e.g., elements of the atmosphere). Therefore, utilizing ion implantation may be an advantageous cost effective and non-hazardous approach of manufacturing and/or filling (e.g., with diffusible material) the examples described herein.

In some examples, the cavity 11' and/or 111' of the cell 100 and/or 400 is formed by creating the gap 11 and/or 111 or hole in one or more of the substrate layers (e.g., the layer 10, 20, 30, 110 and/or 120) using an etching process. The cavity 11' and/or 111' may be formed in a semiconducting substrate similar to processes used in photolithographically defined etching. As described above, the cavity 11' and/or 111' may be later used to deposit and/or receive reactive gas(es).

The first layer 10 and/or 110 having the gap 11 and/or 111 and the second layer 20 and/or 120 and/or the third layer 30 may be coupled and/or joined together using anodic wafer bonding technology to form the cavity 11' and/or 111' (e.g., interioraly positioned). After coupling, the cavity 11' and/or 111' is sealed (e.g., hermetically sealed) from exterior space and/or the atmosphere.

Once sealed, the material deposited in the reservoir area 15 and/or 115 may be driven out of the reservoir area 15 and/or 115 to the cavity 11' and/or 111' by diffusion (e.g., temperature induced diffusion). The cell 100 and/or 400 and/or the material within the reservoir area 15 and/or 115 may be heated to achieve and/or obtain a desired concentration of the reactive gas within the cavity 11' and/or 111'.

The cell 100 and/or 400 may be associated with a time standard or frequency standard. Additionally, the cell 100 and/or 400 may be configured to obtain a predetermined concentration of gaseous material in the cavity 11' and/or 111' using controlled outward diffusion of a material corresponding to gas from the reservoir area 15 and/or 115.

The cell 100 and/or 400 may be used in any suitable application. For example, the cell 100 and/or 400 may be included in or used with an atomic clock, a magnetic field sensor, a rotary speed sensor and/or for the synchronization of communications networks or cryptographic keys.

As set forth herein, an example cell having a cavity and a wall surrounding the cavity includes one or more reservoir areas in the wall to receive material. The reservoir area is within the first substrate layer and is not within the cavity. The material is to enter the cavity by diffusion. In some examples, the wall includes at least one layer of semiconductor substrate and the wall hermetically seals the cavity from an exterior environment. In some examples, the material entering the cavity includes a material in a gaseous state. In some examples, the wall includes a translucent area including glass to enable the cavity to be accessible to light. In some examples, the wall includes at least one layer that includes at least one of silicon, a structured ceramic material, or a structured glass ceramic compound material.

In some examples, the wall includes a metal material and includes a heating element 107 and a plurality of substrate layers that are coupled together. In some examples, the example cell includes one or more diffusion barriers adjacent the one or more reservoir areas, the material includes at least one of rubidium or cesium. In some examples, the wall includes at least one wall segment defining a gap associated with the cavity and includes the one or more reservoir areas to contain the material. After the material is introduced into the one or more reservoir areas and the gap has been formed, the material is to diffuse from the one or more reservoir areas into the gap and be present in the gap in a gaseous state.

An example method of manufacturing a cell having a cavity and a wall surrounding the cavity includes depositing material in at least a portion of the wall. The material is to be introduced into the cavity by diffusion. In some examples, depositing the material in at least the portion of the wall includes depositing the material in at least the portion of the wall using ion implantation and also includes hermetically sealing the cell using the wall. In some examples, the wall includes a plurality of layers of substrate material at least one of which includes a translucent area 108. In some examples, the method includes obtaining a particular concentration of the material in a gaseous state in the cavity by diffusion.

An example cell includes a first layer including a gap to at least partially define a cavity and a reservoir area to receive material to enter the cavity by diffusion. The example cell includes one or more other layers coupled to the first layer to at least partially define the cavity and to hermetically seal the cavity from an exterior environment. In some examples, the cell includes a diffusion barrier positioned at least partially within the first layer to control the diffusion of the material into the cavity. In some examples, the cell is to be associated with at least one of an atomic clock, a magnetic field sensor, a rotational speed sensor, synchronization of communication networks, or cryptographical keys. In some examples, the cell is to be associated with a time or frequency standard.

An example method of producing a cell includes depositing material into a reservoir area of a first portion of the cell, the first portion defines a gap adjacent the reservoir area. The method includes coupling one or more other portions of the cell to the first portion to hermetically seal the gap and initiating the diffusion of the material from the reservoir area into the gap. In some examples, depositing the material into the reservoir area of the first portion of the cell includes depositing the material into the reservoir area of the first portion of the cell using ion implantation. In some examples, the method includes controlling the diffusion of the material from the reservoir area into the gap using a diffusion barrier positioned within or adjacent to the first portion. In some examples, the method includes obtaining a predetermined concentration of the material in a gaseous state in the gap by controlled diffusion from the reservoir area.

Furthermore, although certain example methods, apparatus and articles of manufacture have been described herein, the scope of coverage of this patent is not limited thereto. On the contrary, this patent covers all methods, apparatus and articles of manufacture fairly falling within the scope of the appended claims either literally or under the doctrine of equivalents.

What is claimed is:

1. A cell, comprising:
    a first substrate layer at least partially defining a cavity having an opening, the first substrate layer comprising:
        a wall; and a reservoir area in the wall of the first substrate layer surrounding the cavity, the reservoir area being within the first substrate layer and not being within the cavity, the reservoir area receives at least one of an alkali metal, or an alkali earth metal by ion implantation, the reservoir area comprising at least one of silicon, a structured ceramic material, glass, or a structured glass ceramic compound material, wherein, after the reservoir area receives at least one of an alkali metal, or an alkali earth metal by ion implantation, the at least one of the alkali metal, or the alkali earth metal enters the cavity by diffusion from the reservoir area,
    a second substrate layer coupled to the first substrate layer and covering the opening of the cavity, the second substrate layer comprising a translucent portion to enable optical access to the cavity; and
    a diffusion barrier immediately adjacent the reservoir area, wherein the wall defines a step and the reservoir area is disposed between the step and the diffusion barrier.

2. The cell as defined in claim 1, wherein the wall comprises at least one layer of a semi-conductor substrate and wherein the cavity is hermetically sealed from an exterior environment.

3. The cell as defined in claim 1, wherein the material entering the cavity comprises a material in a gaseous state.

4. The cell as defined in claim 1, wherein the wall includes a translucent area comprising glass to enable the cavity to be accessible to light.

5. The cell as defined in claim 1, wherein the wall includes at least one layer comprising at least one of silicon, a structured ceramic material, or a structured glass ceramic compound material.

6. The cell as defined in claim 1, wherein the wall comprises a metal material and includes a heating element and a plurality of substrate layers that are coupled together.

7. The cell as defined in claim 1, wherein the wall comprises at least one wall segment defining a gap associated with the cavity, the wall segment including the reservoir area containing, prior to diffusion, the at least one of the alkali metal, or the alkali earth metal, wherein, after the at least one of the alkali metal, or the alkali earth metal is introduced into the reservoir area and the gap has been formed, the at least one of the alkali metal, or the alkali earth metal diffuses from the reservoir area into the gap and is present in the gap in a gaseous state.

8. A method of manufacturing the cell of claim 1, comprising:
    depositing the at least one of the alkali metal, or the alkali earth metal in the reservoir area of the wall using ion implantation, wherein the at least one of the alkali metal, or the alkali earth metal is to be introduced into the cavity by diffusion.

9. The method as defined in claim 8, wherein depositing the at least one of the alkali metal, or the alkali earth metal in the reservoir area of the wall comprises hermetically sealing the cell using the wall.

10. The method as defined in claim 8, wherein the wall comprises a plurality of layers of substrate material at least one of which includes a translucent area.

11. The method as defined in claim 8, further comprising obtaining a particular concentration of the least one of the alkali metal, or the alkali earth metal in a gaseous state in the cavity by diffusion.

12. A cell, comprising:
    a first layer at least partially defining a cavity, the first layer comprising:
        a wall segment, and
        a reservoir area being within the first layer and not being within the cavity, the reservoir area at least partially surrounding the cavity, the reservoir area receives at least one of an alkali metal, or an alkali earth metal by ion implantation, the at least one of the alkali metal, or the alkali earth metal enters the cavity by diffusion from the reservoir area, the reservoir area being disposed in the wall segment of the first layer, the reservoir area comprising at least one of silicon, a structured ceramic material, glass, or a structured glass ceramic compound material;
    one or more other layers coupled to the first layer to at least partially define the cavity and to hermetically seal the cavity from an exterior environment; and
    a diffusion barrier immediately adjacent the reservoir area, wherein the wall segment defines a step and the reservoir area is disposed between the step and the diffusion barrier.

13. The cell as defined in claim 12, wherein the cell is a portion of at least one of an atomic clock, a magnetic field sensor, a rotational speed sensor, synchronization of communication networks, or cryptographical keys.

14. The cell as defined in claim 12, wherein the cell is configured to comply with a time or frequency standard.

15. A method of producing the cell of claim 12, comprising:
    depositing material into the reservoir area of the cell by ion implantation, wherein the first layer defines the cavity adjacent the reservoir area, wherein the material is the at least one of the alkali metal, or the alkali earth metal;

coupling the one or more other layers of the cell to the first layer to hermetically seal the cavity; and initiating the diffusion of the material from the reservoir area into the cavity.

16. The method as defined in claim 15, further comprising controlling the diffusion of the material from the reservoir area into the cavity using the diffusion barrier.

17. The method as defined in claim 15, further comprising obtaining a predetermined concentration of the material in a gaseous state in the cavity by controlled diffusion from the reservoir area.

18. The cell as defined in claim 1, further comprising a third substrate layer covering a second opening of the cavity.

19. A cell, comprising: a housing defining and enclosing a cavity, the housing comprising:
   a wall;
   a reservoir area being within the wall and not being within the cavity, the wall at least partially defining the cavity, the reservoir area comprising at least one of silicon, a structured ceramic material, glass, or a structured glass ceramic compound material, the reservoir area configured to receive at least one of an alkali metal, or an alkali earth metal by ion implantation, wherein, after the reservoir area receives the at least one of the alkali metal, or the alkali earth metal, the at least one of the alkali metal, or the alkali earth metal enters the cavity by diffusion from the reservoir area; and
   a diffusion barrier immediately adjacent the reservoir area, wherein the wall defines a step and the reservoir area is disposed between the step and the diffusion barrier.

20. The cell as defined in claim 19, wherein the housing comprises a first substrate layer coupled to a second substrate layer, the first substrate layer comprising the reservoir area, the second substrate layer comprising a translucent portion to enable optical access to the cavity.

21. The cell as defined in claim 20, further comprising a third substrate layer coupled to the first substrate layer.

22. A cell, comprising:
   a first substrate layer at least partially defining a cavity having an opening, the first substrate layer comprising: a wall; and a reservoir area in the wall of the first substrate layer surrounding the cavity, the reservoir area being within the first substrate layer and not being within the cavity, the reservoir area receives at least one of an alkali metal, or an alkali earth metal by ion implantation, the reservoir area comprising at least one of silicon, a structured ceramic material, glass, or a structured glass ceramic compound material, wherein, after the reservoir area receives at least one of an alkali metal, or an alkali earth metal by ion implantation, the at least one of the alkali metal, or the alkali earth metal enters the cavity by diffusion from the reservoir area, and a second substrate layer coupled to the first substrate layer and covering the opening of the cavity, the second substrate layer comprising a translucent portion to enable optical access to the cavity, wherein the reservoir area comprises a first reservoir area and a second reservoir area, the second reservoir area separated from the first reservoir area; and a reflective layer disposed along a surface of the cavity immediately adjacent the second reservoir area.

23. A cell, comprising:
   a first layer at least partially defining a cavity, the first layer comprising:
      a wall segment, and
      a reservoir area being within the first layer and not being within the cavity, the reservoir area at least partially surrounding the cavity, the reservoir area receives at least one of an alkali metal or, an alkali earth metal by ion implantation, the at least one of the alkali metal or the alkali earth metal enters the cavity by diffusion from the reservoir area, the reservoir area being disposed in the wall segment of the first layer, the reservoir area comprising at least one of silicon, a structured ceramic material, glass, or a structured glass ceramic compound material;
   one or more other layers coupled to the first layer to at least partially define the cavity and to hermetically seal the cavity from an exterior environment, wherein the reservoir area comprises a first reservoir area and a second reservoir area, the second reservoir area separated from the first reservoir area; and
   a reflective layer disposed along a surface of the cavity immediately adjacent the second reservoir area.

24. A cell, comprising: a housing defining and enclosing a cavity, the housing comprising:
   a wall;
   a reservoir area being within the wall and not being within the cavity, the wall at least partially defining the cavity, the reservoir area comprising at least one of silicon, a structured ceramic material, glass, or a structured glass ceramic compound material, the reservoir area configured to receive at least one of an alkali metal or an alkali earth metal by ion implantation, wherein, after the reservoir area receives the at least one of the alkali metal, or the alkali earth metal, the at least one of the alkali metal or the alkali earth metal enters the cavity by diffusion from the reservoir area, wherein the reservoir area comprises a first reservoir area and a second reservoir area, the second reservoir area separated from the first reservoir area; and
   a reflective layer disposed along a surface of the cavity immediately adjacent the second reservoir area.

* * * * *